United States Patent [19]

Vicenzi

[11] Patent Number: 5,559,006
[45] Date of Patent: *Sep. 24, 1996

[54] METHOD FOR SELECTIVELY DEACTIVATING CATALASE WHILE RETAINING DAMINO ACID OXIDASE ACTIVITY

[75] Inventor: Jeffrey T. Vicenzi, Indianapolis, Ind.

[73] Assignee: Eli Lilly and Company, Indianapolis, Ind.

[*] Notice: The term of this patent shall not extend beyond the expiration date of Pat. No. 5,424,203.

[21] Appl. No.: 392,438

[22] Filed: Feb. 22, 1995

Related U.S. Application Data

[62] Division of Ser. No. 212,656, Mar. 11, 1994, Pat. No. 5,424,203, which is a continuation of Ser. No. 83,207, Jun. 24, 1993, abandoned, which is a continuation of Ser. No. 4,210, Jan. 13, 1993, abandoned, which is a continuation of Ser. No. 382,505, Jul. 19, 1989, abandoned.

[51] Int. Cl.$^6$ .............................. C12N 9/02; C12N 9/08; C12N 9/99; C12P 35/00
[52] U.S. Cl. ..................... 435/47; 435/184; 435/189; 435/192; 435/255.1
[58] Field of Search .............................. 435/184, 47, 189, 435/192, 255.1

[56] References Cited

U.S. PATENT DOCUMENTS

| | | | |
|---|---|---|---|
| 3,801,458 | 4/1974 | Fildes et al. | 435/47 |
| 3,821,209 | 6/1974 | Arnold et al. | 540/219 |
| 3,912,589 | 10/1975 | Smith et al. | 435/47 |
| 3,976,546 | 8/1976 | Smith et al. | 435/47 |
| 4,079,180 | 3/1978 | Suzuki et al. | 540/224 |
| 4,394,450 | 7/1983 | Brock et al. | 435/191 |
| 4,745,061 | 5/1988 | Aretz et al. | 435/191 |
| 5,424,203 | 6/1995 | Vicenzi | 435/184 |

OTHER PUBLICATIONS

Dixon and Webb, *Enzymes*, 3rd Ed., Academic Press, pp. 11–12 (1979).
Mazzeo et al., *J.C.S. Perkin I*, p. 2532 (1972).
*Agric. Biol. Chem.*, 45(7) 1561–1567, 1981.
*Hakko to Kogyo*, vol. 38, No. 3, pp. 216–237 (1980).
*Biotechnology Letters*, vol. 9, No. 9, 1987, pp. 625–628, S. F. D'Souza et al.
*J. of Bioscience*, vol. 11, No. 1–4, Mar. 1987, pp. 137–144, A. Deshpande, et al.

*Primary Examiner*—Herbert J. Lilling
*Attorney, Agent, or Firm*—Kathleen R. S. Page; Paul R. Cantrell

[57] ABSTRACT

"A method for selectively deactivating catalase while retaining D-amino acid oxidase activity is disclosed. The catalase and oxidase are both present in whole cells or a cell-free extract. The method comprises combining the whole cells or the cell-free extract with a basic solution at a pH between about 11 and about 12. The catalase activity is eliminated and the oxidase activity is unaffected. This results in the production of a solution which contains oxidase activity but no catalase activity. The whole cells and cell-free extract are preferably from *Triginopsis variabilis*."

5 Claims, No Drawings

METHOD FOR SELECTIVELY DEACTIVATING CATALASE WHILE RETAINING DAMINO ACID OXIDASE ACTIVITY

This application is a division, of application Serial No. 08/212,656, filed Mar. 11, 1994 now U.S. Pat. No. 5,424,203, which is a continuation of application Ser. No. 08/083,207, filed Jun. 24, 1993, now abandoned, which is a continuation of application Ser. No. 08/004,210, filed Jan. 13, 1993, now abandoned, which is a continuation of application Ser. No. 07/382,505, filed Jul. 19, 1989, now abandoned.

Background of the Invention

Enzymatic oxidation of Cephalosporin C (Ceph C) to glutaryl-7-aminocephalosporaic acid (glutaryl-7-ACA) has been shown possible on a laboratory scale. (See, for example, Arnold, et al., U.S. Pat. No. 3,821,209, and Fildes et al., U.S. Pat. No. 3,821,209, incorporated herein by reference.) However, a successful and economically feasible scale up to industrial scale production has historically been problematic.

The above conversion is of great commercial importance as it opens up the possibility for an entirely enzymatic route from Cephalosporin C to -amino-cephalosporanic acid (7-ACA), since enzymes which convert glutaryl-7-ACA to 7-ACA are known. [See, for example Shibuya, et al., "Isolation and properties of 7β-(-4-carboxybutanamido)cephalosporanic Acid Acylase-producing Bacteria," *Agric. Biol. Chem.*, 45(7), 1561–1567, 1981]. Further, another advantage of an enzymatic route to 7-ACA is the utilization of an aqueous production mixture, thereby minimizing the hazardous waste solvents generated in the process.

It is known that in order to obtain a good yield of glutaryl-7-ACA, it is essential that all catalase activity be eliminated from the D-aminoacid oxidase. In the above transformation, Cephalosporin C reacts with D-amino acid oxidase to form a thermally unstable α-keto adipoyl 7-ACA intermediate, which is oxidized in situ by the hydrogen peroxide also produced to the desired glutaryl-7-ACA. However, the naturally-occurring catalase enzyme acts to destroy the hydrogen peroxide. Thus, without a means to deactivate catalase prior to the oxidation, the α-keto adipoyl intermediate is found to decompose, thereby reducing the yield of desired glutaryl-7-ACA to the desired glutaryl-7-ACA. It is possible to chromatographically remove this contaminant but on industrial scale production, chromatography of this magnitude is not a practical alternative. Thus, the only practical solution is to somehow selectively deactivate the catalase.

Others have reported the possibility of using catalase inhibitors such as ascorbic acid, 3-amino-1,2,4 -triazole, sodium cyanide, sodium acetate, sodium formate, sodium fluoride, or sodium azide. Among the above inhibitors, sodium azide is the only one that works well enough to be of practical utility. However, one rather serious drawback to the use of sodium azide, is the formation of a 3-azidomethyl-3-cephem by-product which can be carried over to the final product. This azido contaminant is simply not acceptable in pharmaceutical agents, since the extremely toxic azide ion could possibly be released upon administration to the patient.

SUMMARY OF THE INVENTION

The present invention provides a solution to the long standing problem of reduction of catalase activity in an enzymatic oxidation of Cephalosporin C to glutaryl-7-ACA. According to the present invention, catalase activity can be irreversibly deactivated in the presence of D-aminoacid oxidase enzyme, by treating the whole cells of *Triginopsis variabilis* with base to achieve a pH of about 11 to about 12 in water at room temperature. Most importantly, this treatment has no effect at all on the desirable oxidase enzyme.

Further, a heretofore undescribed esterase enzyme may be inactivated by treatment of the whole cells of *Triginopsis variabilis* with acetone/water, which also serves to permeabilize the cells. The deactivation of esterase enzyme is important since esterase enzyme converts the in situ produced α-keto adipoyl 7-ACA intermediate as well as Ceph C and glutaryl-7-ACA to the 3-desacetyl form which leads to corresponding amounts of desacetyl glutaryl-7-ACA.

DETAILED DESCRIPTION OF THE INVENTION

As one aspect of the present invention there is provided a process for the production of glutaryl- 7-ACA substantially free of desacetyl glutaryl-7-ACA which comprises slurrying whole cells of *Triginopsis variabilis* with an acetone/water mixture.

Further, the present invention provides a method for deactivating catalase enzyme in the presence D-aminoacid oxidase enzyme which comprises raising the pH of an aqueous mixture of catalase and D-aminoacid oxidase to a pH of about 11 to about 12.

The present invention further provides an improved process for the enzymatic conversion of Cephalosporin C to glutaryl-7-ACA, the improvement comprising treatment of whole cells of *Triginopsis varabilis* with base to achieve a pH of about 11 to about 12 prior to utilization of said whole cells of *Triginopsis varabilis* in the enzymatic oxidation of Ceph C to glutaryl-7-ACA.

Alternatively, this aspect of the invention can be applied to the conversion of Cephalosporin C to glutaryl 7-ACA via cell-free extracts of *Triginopsis variabilis* containing the oxidase and catalase. Such cell-free extracts are obtained by conventional means, e.g., sonication of aqueous cell suspensions or lysis. The cell-free extract is then treated as described above for whole cells.

The pH of the above whole cells can then be adjusted to about 7 with a dilute acid such as sulfuric acid and used directly in a Ceph C to glutaryl-7-ACA enzymatic oxidation.

*Triginopsis varabilis* whole cells suitable for use in the above process can be obtained using prior art methodology. In this regard *Triginopsis variabilis* may be obtained from the Central Bureau voor Schimmelcultur, Baarn, Holland, under culture number CBS 4095.

In the above process, *Triginopsis variabilis* whole cell paste is slurried with a 90%–50% water/acetone (preferably 2:1, v:v) mixture and treated with an antifoaming agent such as Dow Antifoam A™. This mixture is generally stirred for about 2 hours at 20–25° C. This procedure eliminates greater than 90% of esterase activity and increases apparent oxidase activity about ten-fold. The acetone may be removed by evaporation or by diafiltration on a ceramic or any type cross-flow filter. This process also serves to permeabilize the cells (or as others have described, to "activate" the cells). Prior art processes teach the permeabilization with inter alia, acetone, but the presence of the esterase and its contribution to the coproduction of a 3-desacetyl-7-ACA contaminant is only now appreciated. Thus, this prior art method of permeabilizing the whole cells now has the heretofore unappreciated aspect of esterase deactivation.

The cell/water slurry is then treated with an alkali metal hydroxide such as sodium hydroxide, potassium hydroxide, or some other common base until the pH is about 11 to about 12, and the mixture stirred for 2 hours at 20–25° C. Preferably, sodium hydroxide is employed at a concentration of about two normal. This procedure removes all detectable catalase activity with no effect on oxidase activity. The reaction mixture is then adjusted to about 7 with a dilute acid such as 20% sulfuric acid.

The cell/water slurry can then be use directly in the enzymatic oxidation of Ceph C to glutaryl-7ACA. Generally, yields of 90%±2% can be obtained on a pilot plant scale using the esterase/catalase-deactivated whole cells of *Triginopsis variablis*.

EXPERIMENTAL SECTION

Example 1—General Procedure

Oxidation of Ceph C Using Whole Cells of *Triginopsis variablis*.

A mixture of 1.4 kg of wet triginopsis cell paste (0.42 kg dry wt), 2.1 liters water, 1.08 liters acetone, and 2 ml Dow Antifoam A™ is stirred for 2 hours at 20–25°. This treatment generally eliminates >90% of esterase activity and increases apparent oxidase activity 10 fold. Acetone can be removed by evaporation under vacuum or by diafiltration on crossflow filter.

The pH of cell/water slurry is then adjusted to 11.0 with 2N sodium hydroxide and the reaction mixture stirred for 2 hours at 20–25° C. This treatment removed all detectable catalase activity. The pH was adjusted after 2 hours to 7 with 20% sulfuric acid.

A mixture of the cell/water slurry from above with Dow Antifoam A™ and 1.4 kg of sodium Ceph C (other salts can be used as well as Ceph C) is treated with bubbling pure oxygen to keep reaction mixture saturated with oxygen. The temperature is maintained at 23° C. and pH at 7.1. The reaction is generally complete in 60–120 minutes depending on specific activity of yeast cells.

When reaction is complete, the reaction mixture is concentrated to ⅓ of original volume on ceramic crossflow filters and then diafiltered with 1 volume of water. The reaction mixture is sparged with nitrogen during concentration to help preserve enzymatic activity. The permeate is kept as product while the concentrated cell slurry is recycled for reuse.

Example 2

A 12 g sample of a wet paste of *Trigonopsis variabilis*, which had been permeabilized with acetone/water in a manner analogous to that used above, was slurried in 50 ml of water. The pH was then adjusted to 11 with 2N NaOH and the reaction mixture stirred at room temperature for 1 h, 45 min. The pH of the reaction mixture was then adjusted to pH 6.5 with 1N HCl and the whole cells were used in an enzymatic conversion of Ceph C to glutaryl-7ACA.

The whole cells were then slurried with 14.04 g of sodium Ceph C (at approximately 84% purity) and 300 ml of water, while bubbling into the reaction mixture pure oxygen. After 72 minutes and subsequent workup, the experiment provided 92.8% (in situ yield) of glutaryl- 7-ACA.

I claim:

1. A method for selectively deactivating catalase while retaining D-amino acid oxidase activity, wherein the catalase and the D-amino acid oxidase are both present in whole cells or a cell-free extract, said method comprising combining said whole cells or said cell-free extract with a basic solution at a pH between about 11 and about 12, whereby catalase activity is eliminated and oxidase activity is unaffected to produce a solution containing said oxidase without catalase being present, and lowering the pH of the solution containing said oxidase to provide a D-amino acid oxidase capable of enzymatic oxidation of cephalosporin C to glutaryl-7-ACA in high yields.

2. The method of claim 1, wherein the whole cells are *Triginopsis variabilis* cells or a cell-free extract therefrom.

3. The method of claim 2 further comprising the step of treating the whole cells of *Triginopsis variabilis* with acetone/water prior to selectively deactivating said catalase.

4. A process for enzymatic oxidation of cephalosporin C to glutaryl-7-ACA, comprising contacting the treated whole cells of claim 3 with cephalosporin C to produce glutaryl-7-ACA.

5. A process of enzymatic oxidation of cephalosporin C to glutaryl-7-ACA, comprising contacting the cell-free extract of claim 2 with cephalosporin C to produce glutaryl-7-ACA.

\* \* \* \* \*